(12) United States Patent
Baynham

(10) Patent No.: US 9,211,197 B2
(45) Date of Patent: Dec. 15, 2015

(54) EXPANDABLE CORPECTOMY DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 6 days.

(21) Appl. No.: 14/214,397

(22) Filed: Mar. 14, 2014

(65) Prior Publication Data

US 2014/0277470 A1  Sep. 18, 2014

Related U.S. Application Data

(60) Provisional application No. 61/785,423, filed on Mar. 14, 2013.

(51) Int. Cl.
*A61F 2/44* (2006.01)
*A61F 2/30* (2006.01)

(52) U.S. Cl.
CPC . *A61F 2/447* (2013.01); *A61F 2/44* (2013.01); *A61F 2/4455* (2013.01); *A61F 2002/30364* (2013.01); *A61F 2002/30505* (2013.01); *A61F 2002/30523* (2013.01); *A61F 2002/30528* (2013.01); *A61F 2002/30551* (2013.01); *A61F 2002/30556* (2013.01); *A61F 2002/30579* (2013.01); *A61F 2002/30601* (2013.01); *A61F 2002/4475* (2013.01)

(58) Field of Classification Search
CPC .. A61F 2/44; A61F 2/447; A61F 2002/30523
See application file for complete search history.

(56) References Cited

U.S. PATENT DOCUMENTS

| | | | |
|---|---|---|---|
| 5,171,278 A | 12/1992 | Pisharodi | |
| 5,290,312 A | 3/1994 | Kojimoto et al. | |
| 6,176,881 B1 * | 1/2001 | Schar et al. | 623/17.11 |
| 6,200,348 B1 * | 3/2001 | Biedermann et al. | 623/17.11 |
| 6,419,705 B1 | 7/2002 | Erickson | |
| 6,524,341 B2 | 2/2003 | Lang et al. | |
| 6,730,088 B2 | 5/2004 | Yeh | |
| 6,866,682 B1 | 3/2005 | An et al. | |
| 7,029,498 B2 | 4/2006 | Boehm et al. | |
| 7,544,208 B1 | 6/2009 | Mueller et al. | |
| 7,674,296 B2 | 3/2010 | Rhoda et al. | |
| 8,062,366 B2 | 11/2011 | Melkent | |
| 8,197,546 B2 | 6/2012 | Doubler et al. | |
| 2006/0004447 A1 | 1/2006 | Mastrorio et al. | |
| 2006/0058879 A1 | 3/2006 | Metz-Stavenhagen | |
| 2007/0255408 A1 | 11/2007 | Castleman et al. | |
| 2007/0255409 A1 | 11/2007 | Dickson et al. | |
| 2009/0204215 A1 * | 8/2009 | McClintock et al. | 623/17.11 |
| 2010/0324687 A1 * | 12/2010 | Melkent et al. | 623/17.16 |
| 2013/0053965 A1 * | 2/2013 | Metz-Stavenhagen | 623/17.16 |
| 2014/0052249 A1 * | 2/2014 | Metz-Stavenhagen | 623/17.11 |
| 2014/0107787 A1 * | 4/2014 | Stinchfield et al. | 623/17.16 |

* cited by examiner

*Primary Examiner* — Ellen C Hammond
(74) *Attorney, Agent, or Firm* — McHale & Slavin, P.A.

(57) ABSTRACT

The instant invention is a longitudinally adjustable corpectomy device which fits within the intervertebral distracted channel. A ratchet mechanism allows for an extendable member to adjust to a longer length to accommodate a distracted channel. The ratchet type mechanism allows the members to move in a unidirectional movement to prevent the two members from contracting once expanded.

9 Claims, 13 Drawing Sheets

EXPANDABLE CORPECTOMY DEVICE

PRIORITY CLAIM

In accordance with 37 C.F.R. 1.76, a claim of priority is included in an Application Data Sheet filed concurrently herewith. Accordingly, the present invention claims priority to U.S. provisional patent application Ser. No. 61/785,423, filed on Mar. 14, 2013, entitled "EXPANDABLE CORPECTOMY DEVICE", the contents of which are hereby expressly incorporated herein by reference.

FIELD OF THE INVENTION

The invention generally relates to improvements to vertebral implants and, more particularly, to a longitudinally expandable vertebral implant including telescoping sections configured for incremental expansion by a ratchet expander for ease of securement at any desired increment in situ.

BACKGROUND OF THE INVENTION

The spine consists of vertebrae that are categorized into sections known as the cervical, thoracic and lumbar section in a flexible arranged column. The vertebrae are separated by small cartilaginous cushions known as intervertebral discs. Intervertebral discs are oblate spherical structures that maintain the space between adjacent vertebrae. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc wherein a mucoprotein gel serves to absorb shocks.

Deterioration of an intervertebral disc results in limited mobility and can cause severe pain. For instance, normal aging causes the nucleus pulposus to lose fluid and contract in volume resulting in a reduction in the intervertebral space. Any reduction of space between adjacent vertebrae may put pressure on the nerves of the spinal column. Further, a reduction in volume of the nucleus pulposus reduces the disc's ability to absorb shock which can result in disc herniation. The bulge of a herniated disc may also put pressure on nearby nerve structures resulting in pain as well as diminished range of motion.

Surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc.

In order to reduce the pain associated with the movement of the intervertebral joint, surgical intervention is often indicated as a means to alleviate pressure upon the spinal cord while concomitantly stabilizing the associated vertebrae. This involves a surgical procedure to distract the disc and or vertebra, or portions thereof, and the insertion of bone fusing material into the cavity of the opposing vertebra. Corpectomy devices have been developed to help support the spine and maintain the normal spacing between opposing vertebrae. Some of these devices may be packed with fusing material to ensure solid bone growth between the two vertebrae. Typically, corpectomy devices are manufactured at various heights requiring that a cavity between opposing vertebrae be distracted to a dimension corresponding to the sized corpectomy device. The surgical procedure to prepare the implant site can be difficult and lengthy. Moreover, the procedure can increase risk of trauma to the tissues surrounding of the implant site.

SUMMARY OF THE INVENTION

The instant invention is a longitudinally adjustable corpectomy device which fits within the intervertebral distracted channel. The device includes a means for engaging an extendable member to accommodate the distracted channel. An expanding member moves in relation to a base member in accordance with a rack and pinion type operation. The ratchet mechanism prevents the two members from contracting once expanded.

An objective of the instant invention to provide a corpectomy device that may be adjusted within the intervertebral cavity or adjusted in situ within the cavity.

It is a further objective of the instant invention to provide an expandable corpectomy which can be expanded by use of a rack rotated by a removable shaft.

Yet another objective of the instant invention is to provide vertebra engagable endplates which are arranged to pivot and self adjust.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
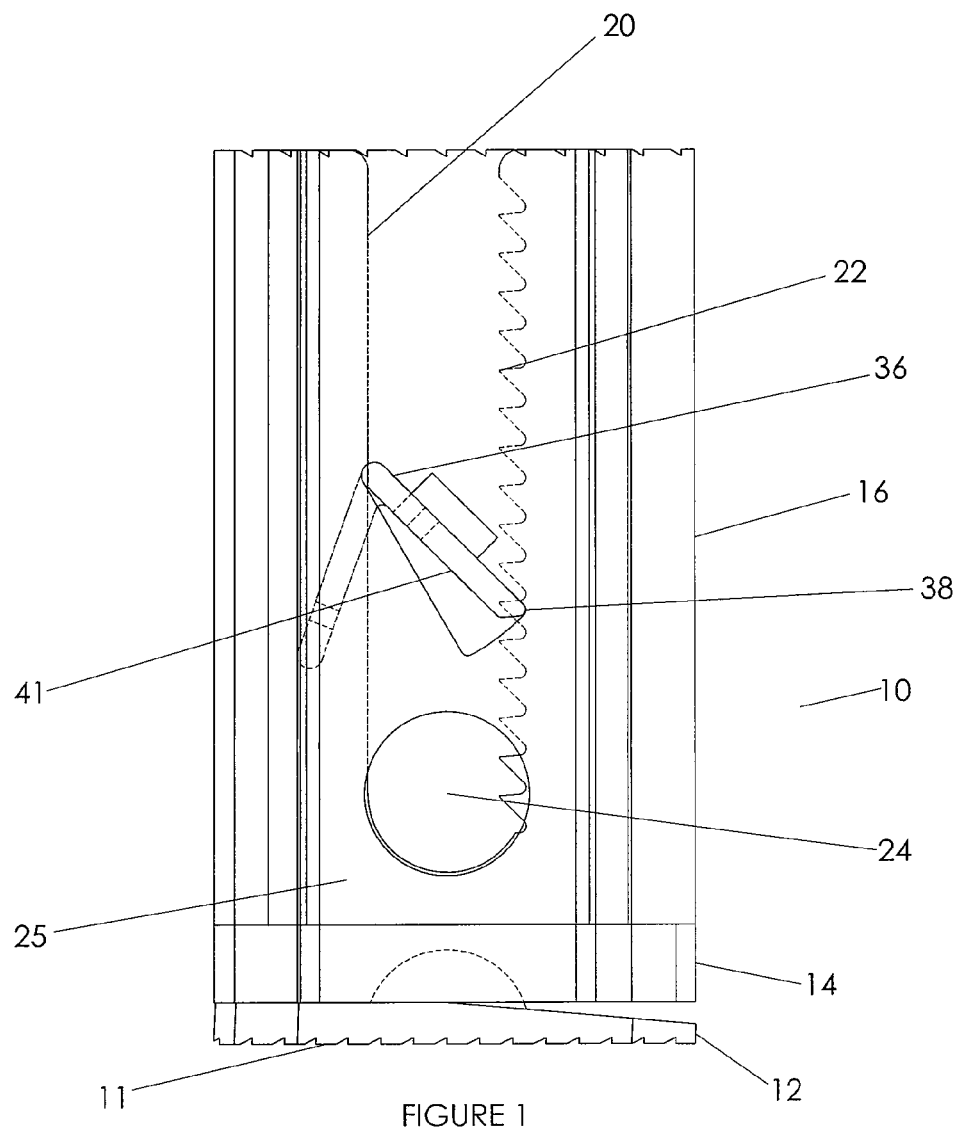
FIG. 1 is a side view of the corpectomy device in a compressed position with the pivoting endplate angled forward.

Referring now to the Figures, set forth is the corpectomy device 10 in a compressed position with the pivoting endplate 12 angled forward. The corpectomy implant device 10 is defined by a base member 14 telescopingly received into an expansion member 16. The base member 14 is formed from a housing having a lower end 15 with a first 17 and second 19 side walls extending from said lower end 15. Said base member include end walls 21 and 23 positioned between said first and second side walls 17,19 each having a centrally disposed U-shaped slot 18 formed therein extending from the lower end along a length of the end walls with a first edge 20 of said slot 18 non-engaging and a second edge 22 lined with an engaging edge, preferably directional ratchet teeth 22. Lower endplate 12 can be inserted into the open end of the base member 14, the lower endplate having a surface 11 for use in bone engagement.

The expansion member 16 is formed from housing having first and second side walls 25 and 27 and first and second end walls 29 and 31, the four walls constructed and arranged to encompass said base member walls. Side wall 25 includes an aperture 24 sized to permit insertion of pinion tool 30 having a shoulder 32 that allows ease of rotation by bearing upon the side wall 25 with a pinion for engagement of the ratchet teeth 22. Rotation of the pinion tool 30 provides extension of the expansion member 16 from the base member 14 as the pinion tool is limited in movement with the expansion member 16 by the size of the aperture 24.

Positioned with the base member is a spring loaded biasing ratchet assembly 36 having a pair of engagement prongs 38 and 40 that engage the ratchet teeth 22. The biasing ratchet assembly 36 includes having a biasing member 41 that engages an inner surface of the base member 14 expanding the engagement prongs 38 and 40 against the ratchet teeth 22 wherein the spacing of the extension member from the base member is unidirectional to prohibit compression of the structure once positioned. The expansion member 16 permits the device to expand relative to the base member 14 and overall longitudinal dimension of the device. Upper endplate 42 can be inserted into the open end of the expansion member 16, the upper endplate having a surface 44 for use in bone engagement.

Figure 2:
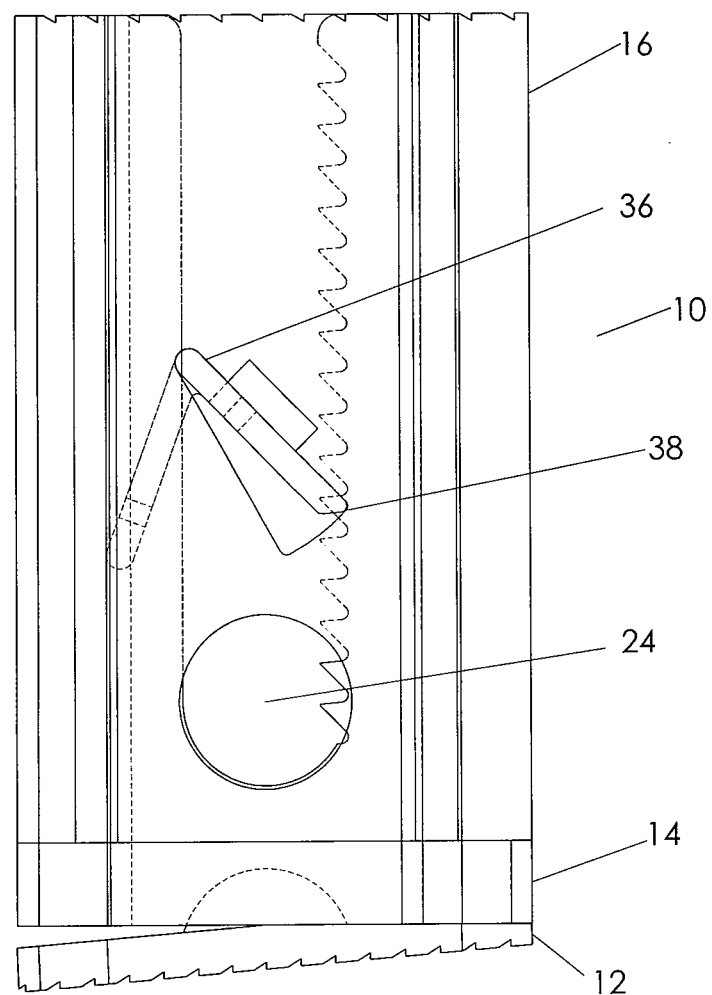
FIG. 2 is a side view of the corpectomy device in a compressed position with the pivoting endplate angled backward.
Figure 3:
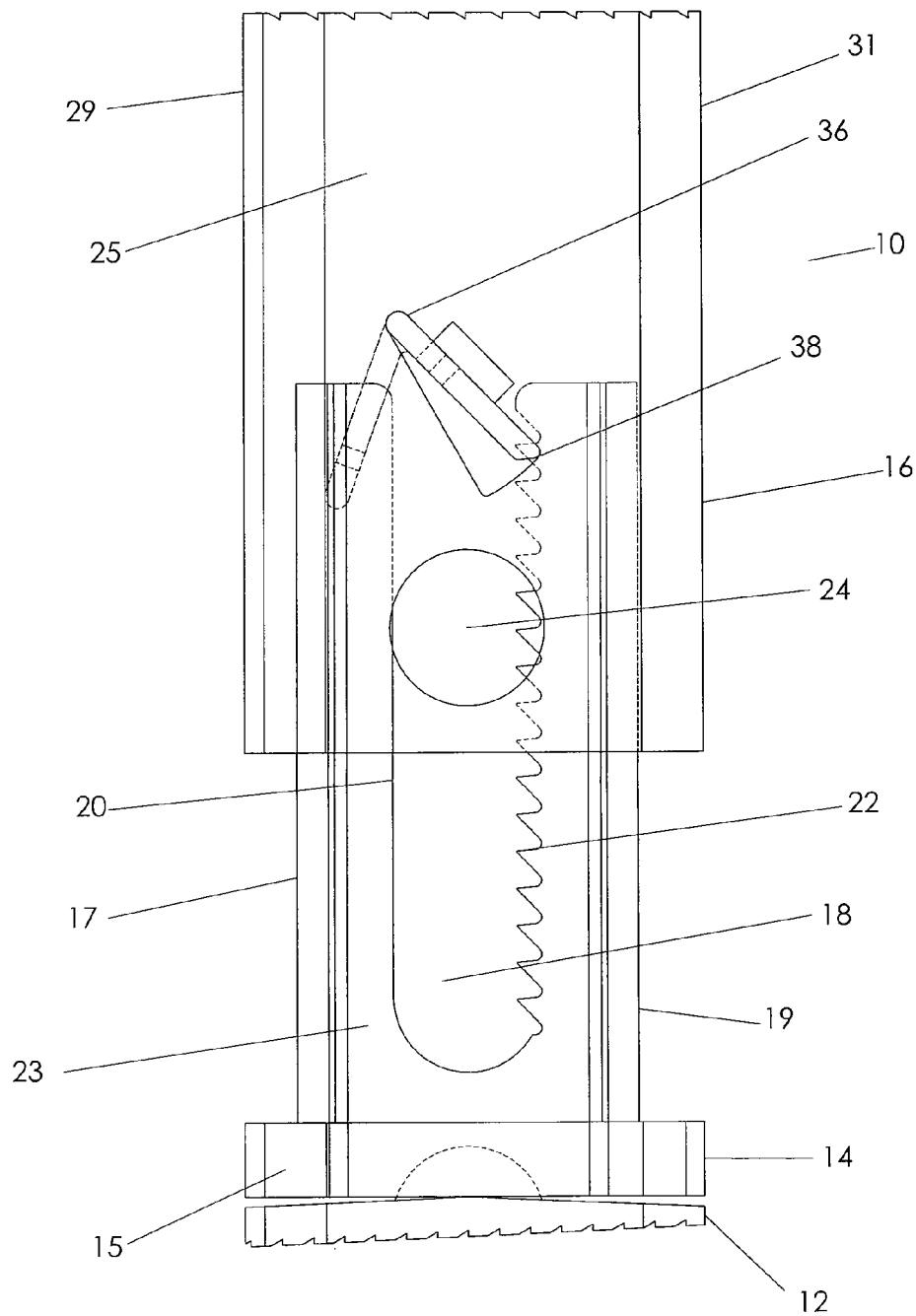
FIG. 3 is a side view of the corpectomy device in a raised position with the pivoting endplate centered; backward.
Figure 12:
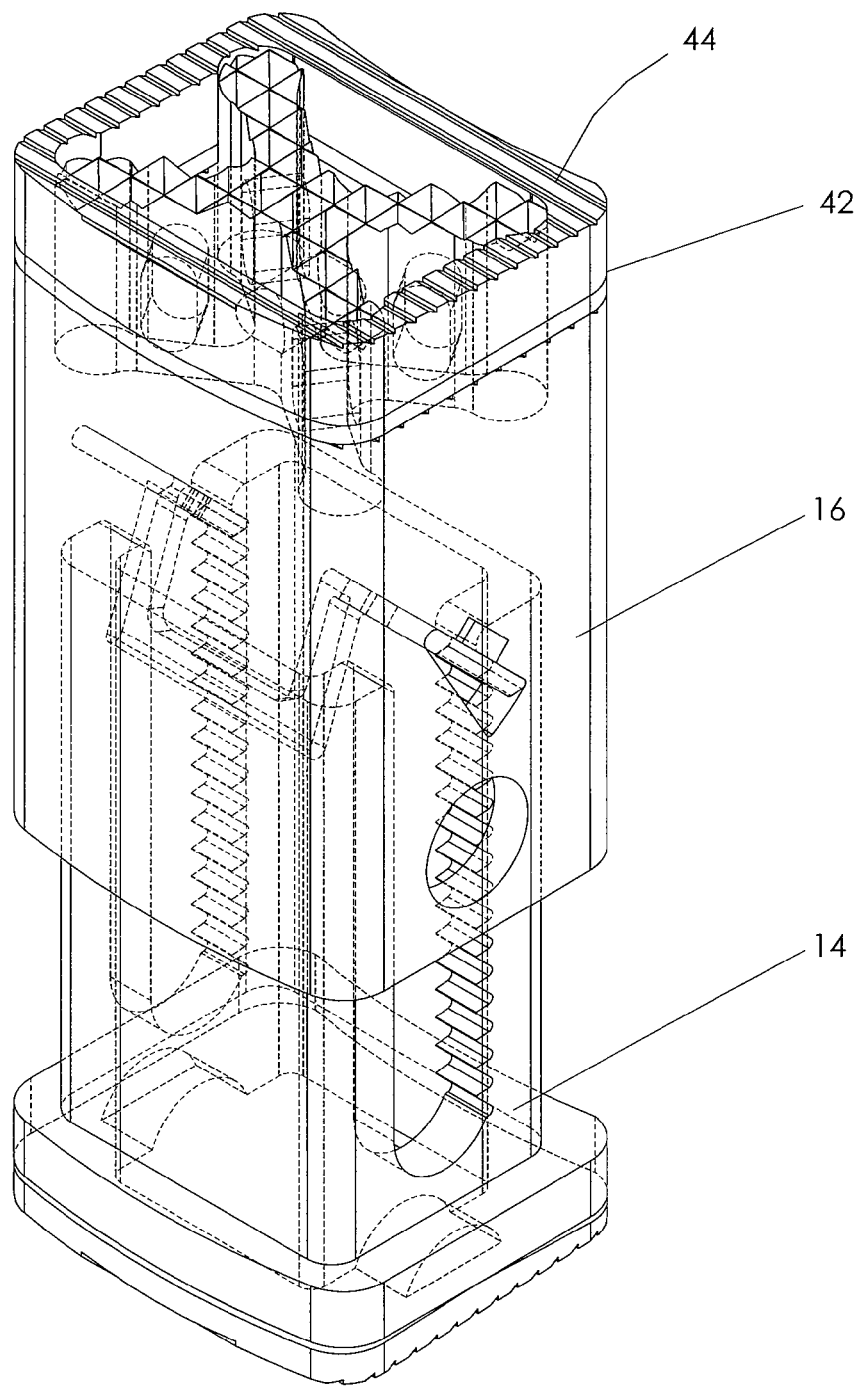
FIG. 12 is a pictorial view depicting the corpectomy device with a top endplate.
Figure 13:
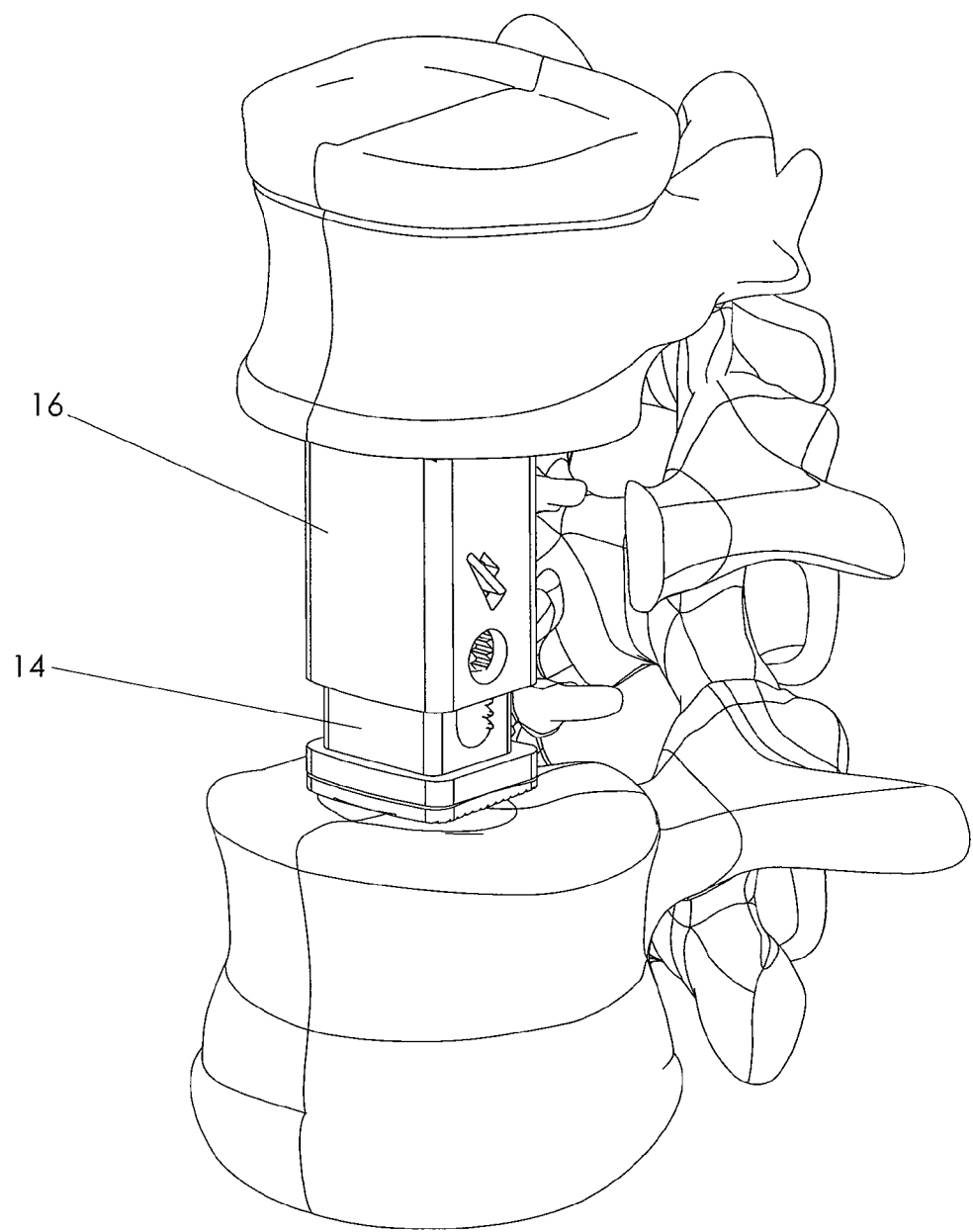
FIG. 13 is a pictorial view of the corpectomy device in position.

The endplates 12 and 42 may be interchangeably connected or permanently attached, such as laser welded, to the corpectomy device. These endplates may be of any desired shape, size or thickness. For example, the endplate 42 of FIG. 12 is substantially flat with engagement teeth 44 forming a pattern allowing bone growth material to pass through. In FIGS. 1-3 the endplate 12 can be moved at an angle that will allow the implant to restore the normal curvature of the spine after the corpectomy device is installed. Moreover, the shape may or may not correspond to the cross-sectional shape and size (foot-print) of the base. In those instances where the patient presents unusual physiology, such as curvature of the spine (lordosis or kyphosis), additional physiology compensating members may be interposed with the respective endplates. These compensating members allow the corpectomy implant device 10 to take on a more arcuate shape thereby conforming more closely with the existing spinal configuration.

FIG. 2 is a side view of the corpectomy implant device 10 in a compressed position having expansion member 16 placed over the insert of base member 14 with the pivoting endplate 12 angled backward. FIG. 3 is a side view of the corpectomy implant device 10 in a raised position with the pivoting endplate 12 centered.

Figure 4:
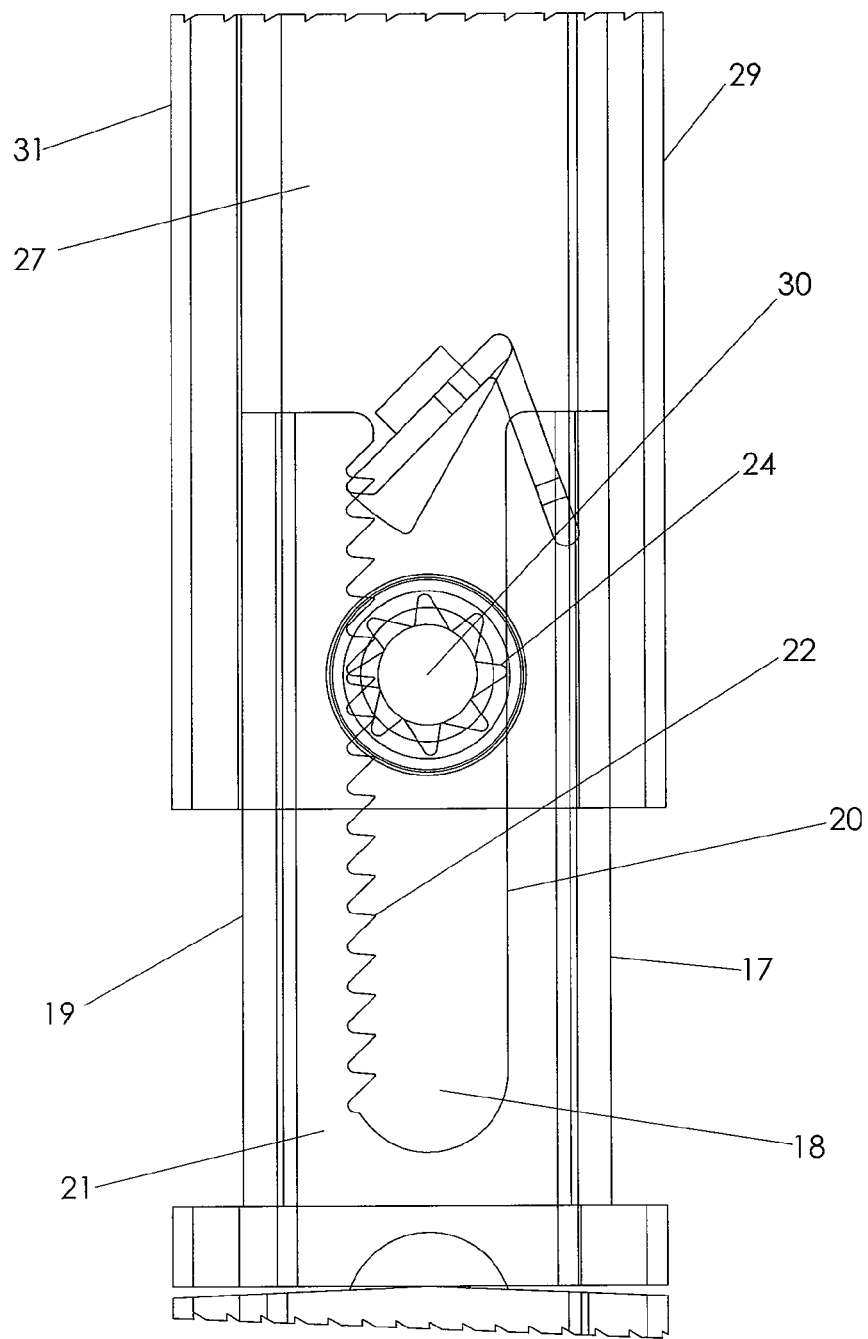
FIG. 4 is the opposite side view of FIG. 3 depicting the pinion driver.
Figure 5:
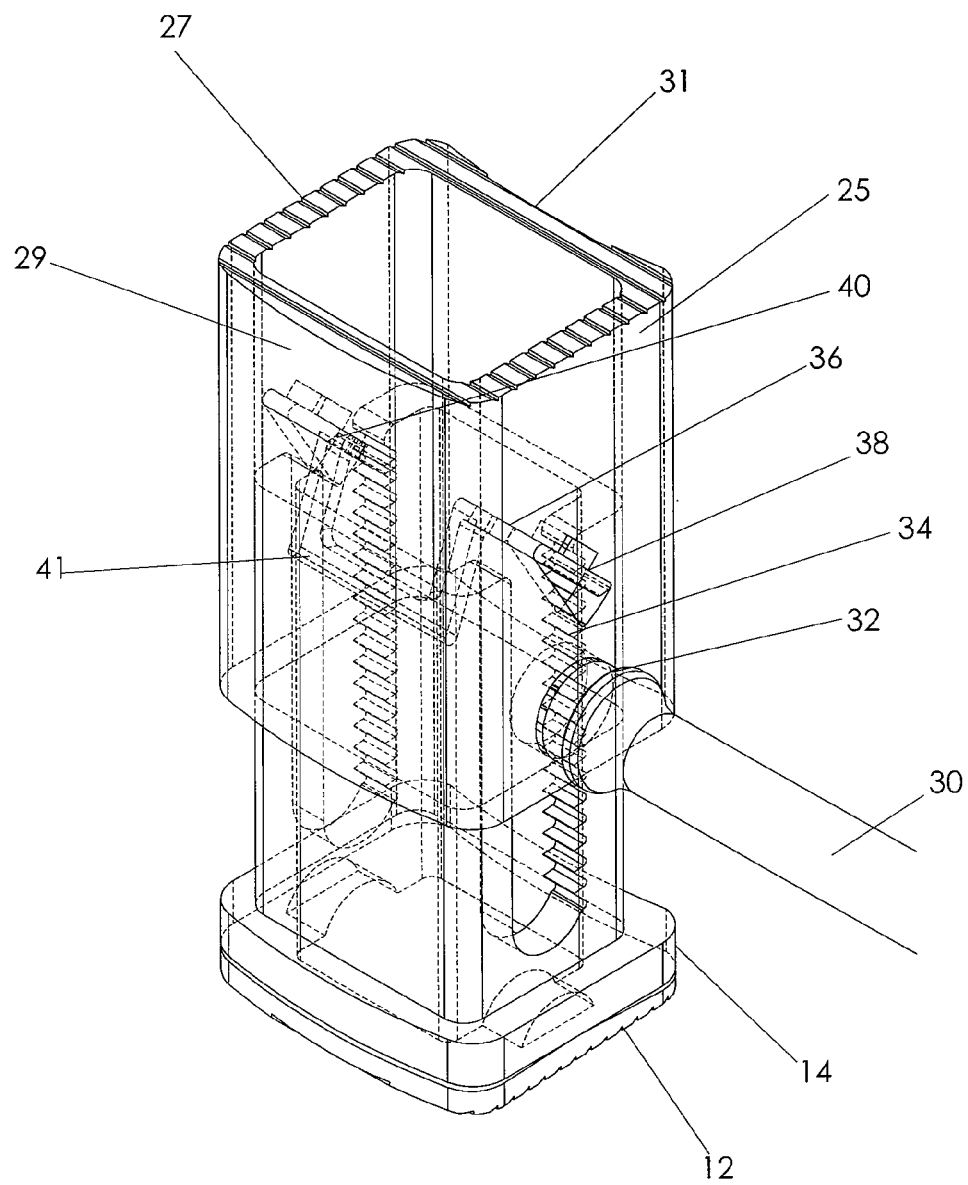
FIG. 5 is the perspective view illustrating the ratchet mechanism for use in locking the members in position.
Figure 6:
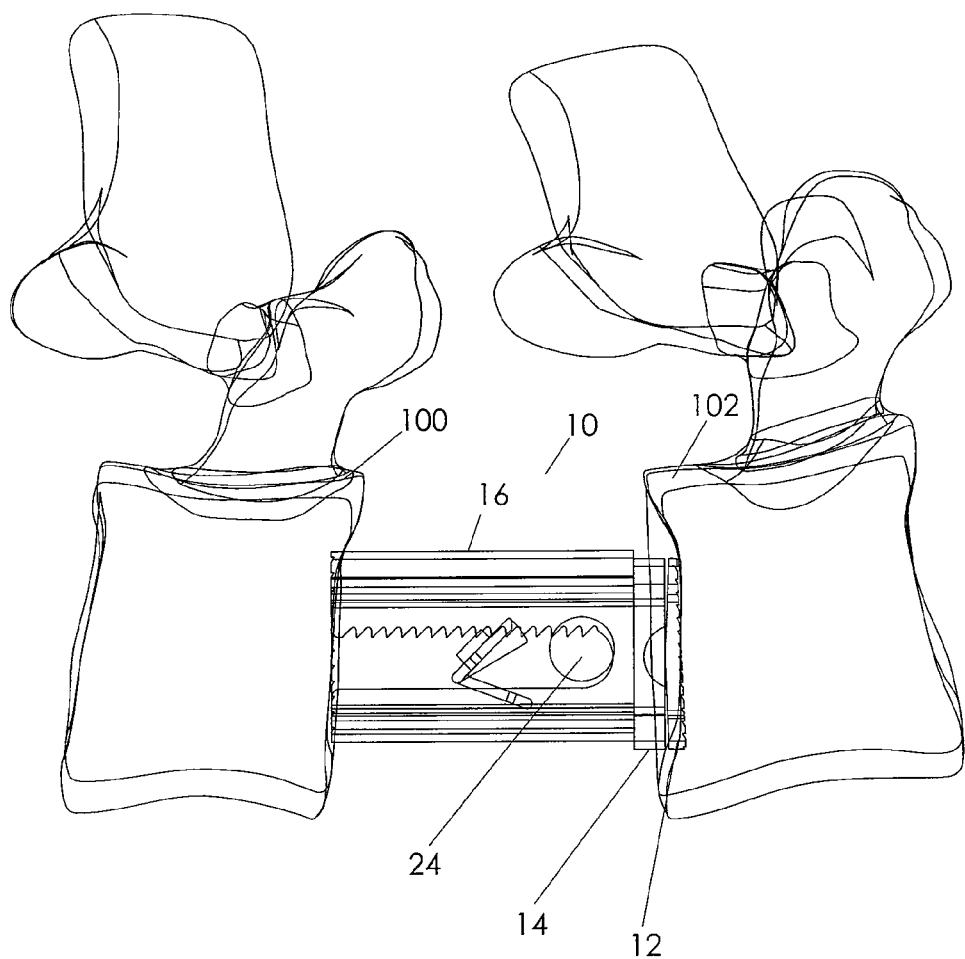
FIG. 6 is a pictorial view depicting the corpectomy device between vertebra in a compressed position.
Figure 7:
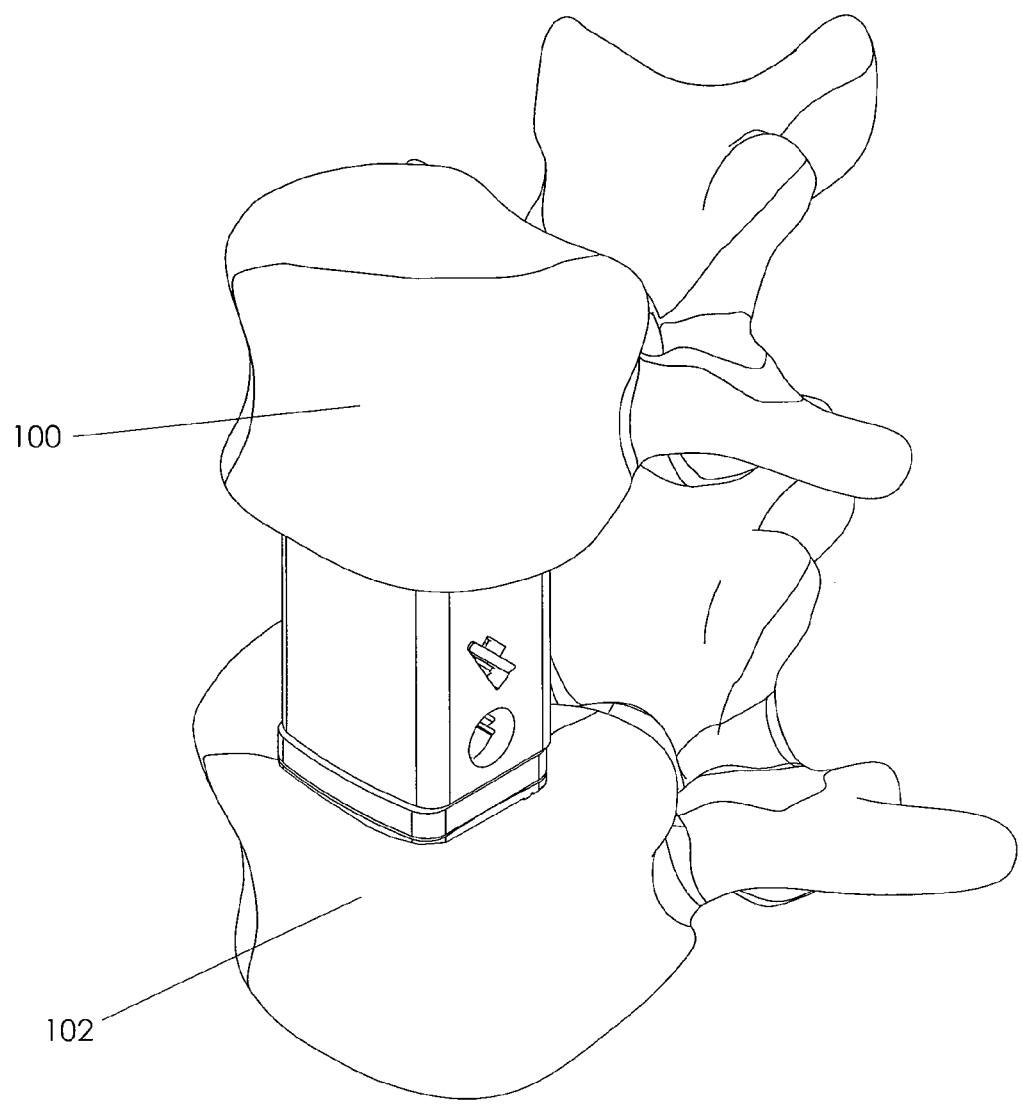
FIG. 7 is another pictorial view of FIG. 6 from a different perspective.
Figure 8:
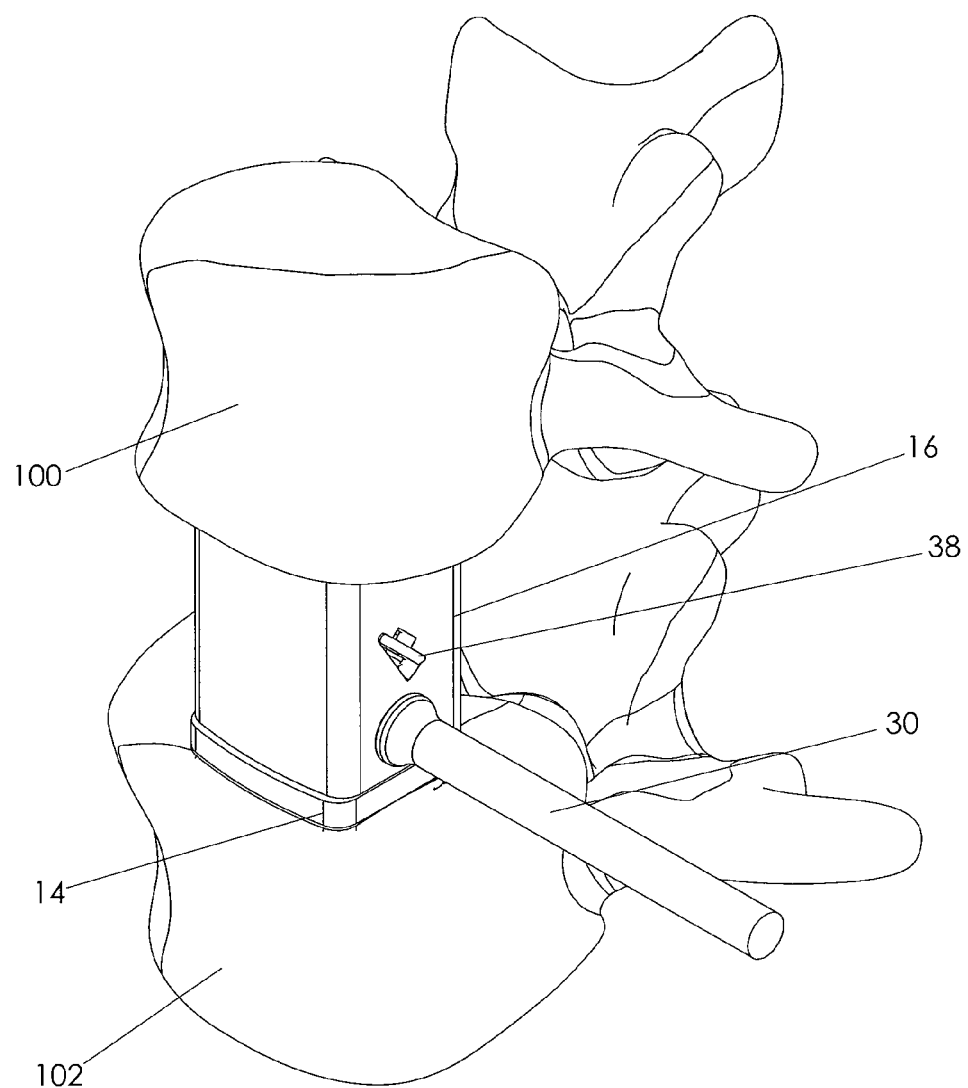
FIG. 8 is view of FIG. 7 with a pinion driver.

FIG. 4 is the opposite side view of FIG. 3 depicting the pinion driver 30 inserted into aperture 24. FIG. 5 is the reverse perspective view illustrating the biasing ratchet mechanism 36 for use in locking the base member 14 and the expansion member 16 in a raised position.

FIGS. 6-8 and 13 are pictorial views depicting the corpectomy implant device 10 between vertebra 100 and 102 in a compressed position.

Figure 9:
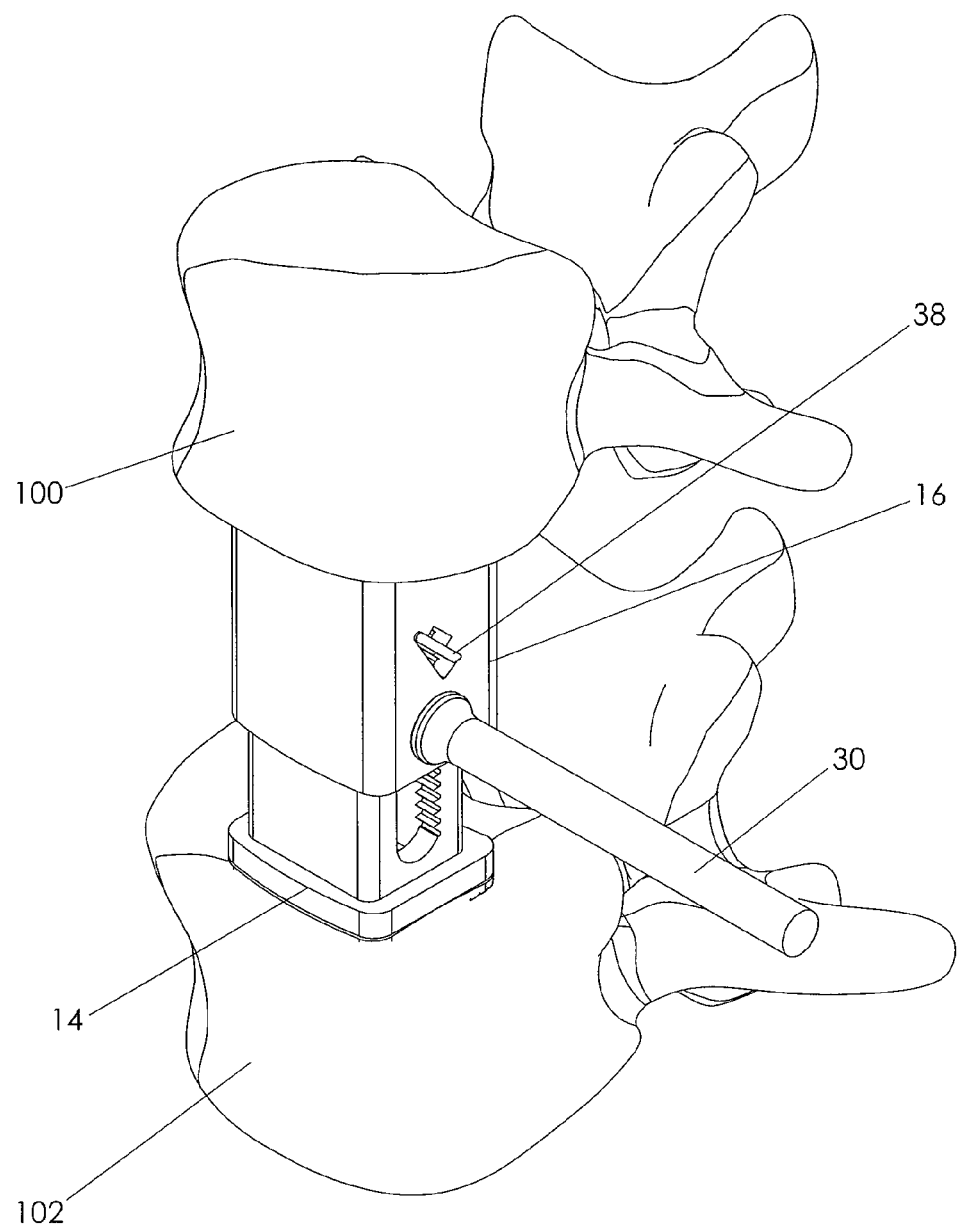
FIG. 9 is view of FIG. 8 upon rotation of the pinion driver.
Figure 10:
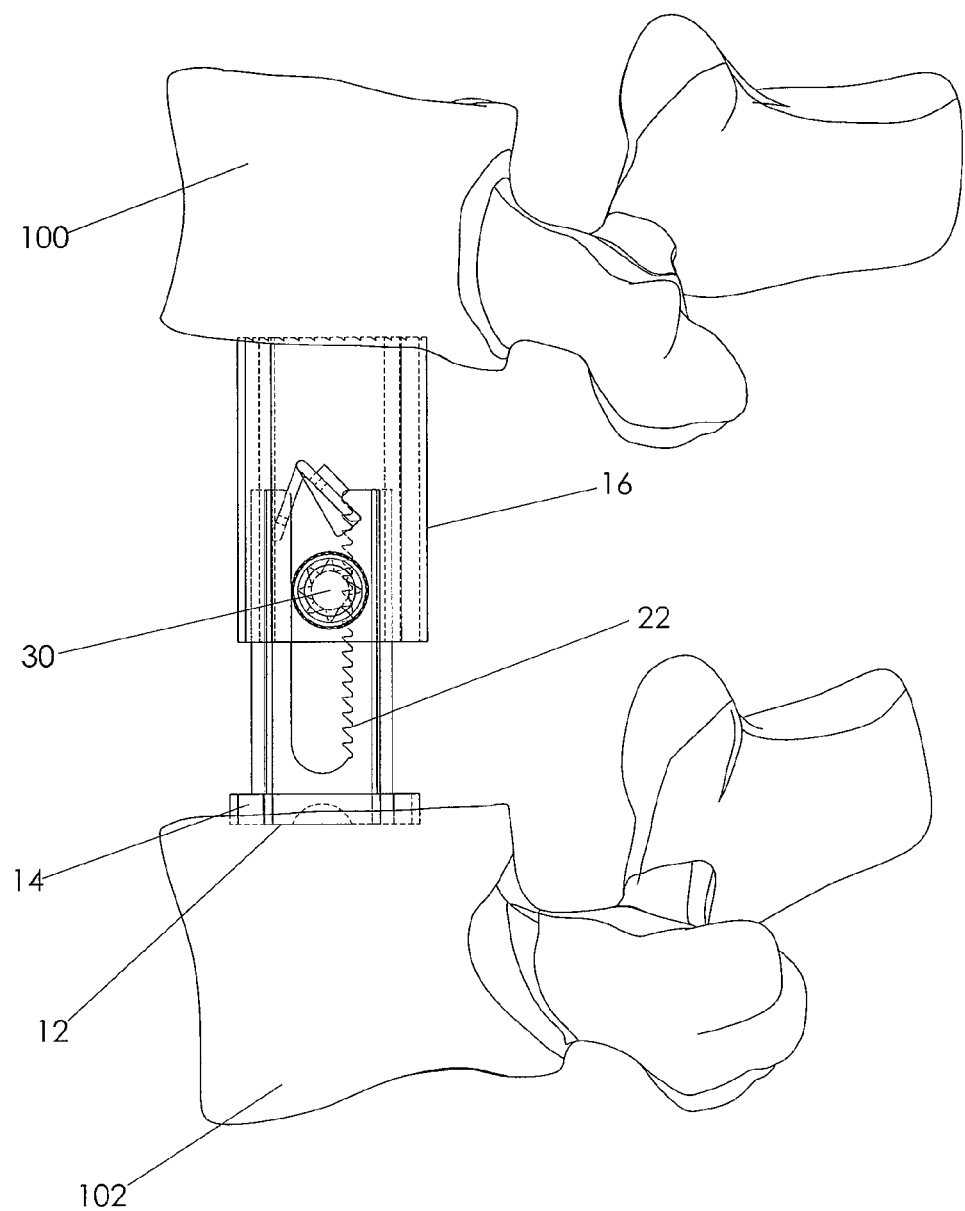
FIG. 10 is a pictorial view depicting the corpectomy device between vertebra in an expanded position.
Figure 11:
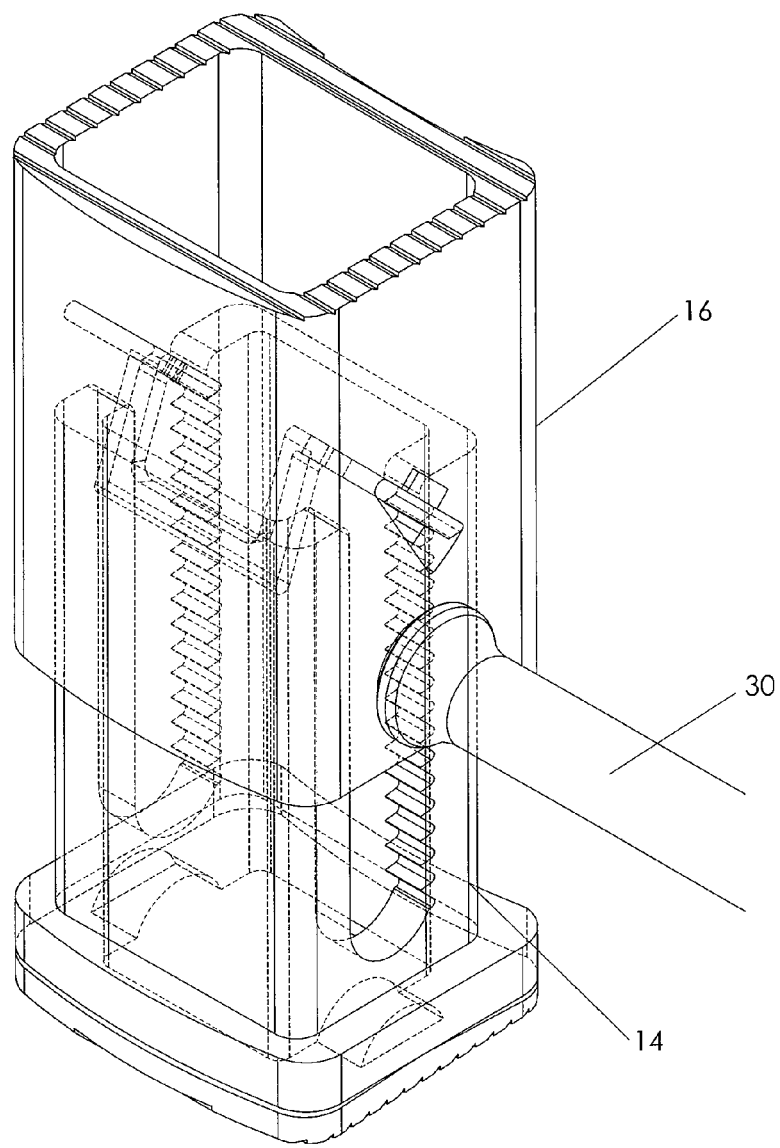
FIG. 11 is a pictorial view depicting the ratchet mechanism of the corpectomy device.

FIGS. 9-11 depict the device in an expanded state with the pinion driver 30 used to raise the expansion member 16 over the base member 14.

Accordingly, in preferred embodiments, a corpectomy device comprises a base member, an expansion member, an upper or lower endplate.

In another preferred embodiment, the base member comprises a slot having a first side wall and a second side wall, wherein the first side wall is smooth and the second side wall comprises one or more teeth, spikes or jagged edges.

In another preferred embodiment, the expansion member comprises an aperture for receiving a pinion tool having a first shoulder wherein the first shoulder is smooth, and a second shoulder for engagement of the base member.

In yet another preferred embodiment, the corpectomy device comprises a ratchet, the ratchet comprising at least one engagement prong, a biasing member or combinations thereof.

In yet another preferred embodiment, the upper and lower endplates are interchangeable and comprise patterns, dimensions, shapes, smooth surfaces, grooved surfaces, rough surfaces, or mobility for engaging a vertebra.

Embodiments of the invention are also directed to methods for manipulating the distance between vertebrae in a patient in need thereof.

Accordingly, in a preferred embodiment, a method of manipulating the distance between adjacent vertebrae in a patient, comprising surgically inserting an expandable corpectomy device into an intervertebral cavity, the corpectomy device comprising an upper endplate, a lower endplate, a base member wherein the base member is telescopingly receivable into an expansion member; the base member comprising a slot having a first side wall that is smooth and a second side wall lined with teeth; the expansion member having an aperture for receiving a pinion tool for increasing longitudinal distances of the expansion member relative to the base member.

In some preferred embodiments, the distances between the teeth in the second side wall of the base member aperture are sized so that the expansion can occur by desired increments.

In another preferred embodiment, the corpectomy device comprises a spring loaded biasing ratchet having a pair of engagement prongs for engaging the second side wall of the aperture of the base member and a biasing member for engaging an inner surface of the base member.

In other preferred embodiments, the upper endplate is insertable into an open end of the expansion member, the upper endplate having a surface for bone engagement. Preferably, the upper and lower endplates are interchangeable and comprise patterns, dimensions, shapes, smooth surfaces, grooved surfaces, rough surfaces, or mobility for engaging a vertebra.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A corpectomy device comprising: a base member formed from a housing having a lower end with first and second side walls spaced apart and extending therefrom, with opposing end walls, at least one end wall having a centrally disposed U-shaped slot extending from the lower end along a length of the opposing end walls, said U-shaped slot having at least one edge having an engaging surface;
   an expansion member having first and second side walls and first and second end walls constructed and arranged to encompass said base member side and end wall and permit telescope expansion thereto, one said side of said expansion member including an aperture placed adjacent to said U-shaped slot;
   a biasing ratchet assembly mounted within said base having at least one engagement prong operatively associated with said engaging surface;
   wherein said aperture is sized to receive a pinion tool for use in extending said expansion member in relation to said base member, said engagement prong insertable into said engaging surface to prevent said expansion member from contracting once telescoped.

2. The corpectomy device according to claim 1 wherein said biasing ratchet includes a biasing spring to maintain said prong against said engaging surface.

3. The corpectomy device according to claim 1 wherein said engaging surface are unidirectional teeth.

4. The corpectomy device according to claim 1, wherein said U-shaped slot is further defined by a non-engaging edge adjacent said engaging surface.

5. The corpectomy device according to claim 1 including an upper endplate securable to an end of said expansion member.

6. The corpectomy device according to claim 5 wherein said upper endplate is pivotably attached to the end of said expansion member.

7. The corpectomy device according to claim 1, including a lower endplate securable to an end of said base member.

8. The corpectomy device according to claim 7 wherein said lower endplate is pivotably attached to the end of said base member.

9. The corpectomy device according to claim 1 including a lower endplate securable to said lower end of said base member and an upper endplate securable to said upper end of said expansion member, said endplates are interchangeable and have an outer surface for engaging vertebra.

* * * * *